(12) United States Patent
Teamey et al.

(10) Patent No.: US 8,845,875 B2
(45) Date of Patent: *Sep. 30, 2014

(54) ELECTROCHEMICAL REDUCTION OF $CO_2$ WITH CO-OXIDATION OF AN ALCOHOL

(71) Applicant: Liquid Light, Inc., Monmouth Junction, NJ (US)

(72) Inventors: Kyle Teamey, Washington, DC (US); Jerry J. Kaczur, North Miami Beach, FL (US); Emily Barton Cole, Houston, TX (US); Paul Majsztrik, Cranbury, NJ (US); Narayanappa Sivasankar, Plainsboro, NJ (US); Andrew B. Bocarsly, Plainsboro, NJ (US)

(73) Assignee: Liquid Light, Inc., Monmouth Junction, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/724,231

(22) Filed: Dec. 21, 2012

(65) Prior Publication Data

US 2013/0140187 A1 Jun. 6, 2013

Related U.S. Application Data

(60) Provisional application No. 61/703,175, filed on Sep. 19, 2012, provisional application No. 61/720,670, (Continued)

(51) Int. Cl.
| | | |
|---|---|---|
| C25B 3/00 | (2006.01) | |
| C25B 1/00 | (2006.01) | |
| C25B 1/24 | (2006.01) | |
| C25B 9/10 | (2006.01) | |
| C07C 51/02 | (2006.01) | |
| C07C 67/08 | (2006.01) | |
| C25B 3/06 | (2006.01) | |
| C25B 9/08 | (2006.01) | |
| C07C 51/367 | (2006.01) | |
| C25B 3/04 | (2006.01) | |
| C07C 29/149 | (2006.01) | |
| C25B 15/08 | (2006.01) | |
| C07C 51/15 | (2006.01) | |
| C25B 3/02 | (2006.01) | |

(52) U.S. Cl.
CPC ............ *C07C 51/367* (2013.01); *C25B 1/24* (2013.01); *C25B 9/10* (2013.01); *C07C 51/02* (2013.01); *C07C 67/08* (2013.01); *C25B 3/06* (2013.01); *C25B 9/08* (2013.01); *C25B 1/00* (2013.01); *C25B 3/04* (2013.01); *C07C 29/149* (2013.01); *C25B 15/08* (2013.01); *C07C 51/15* (2013.01); *C25B 3/02* (2013.01); *C25B 3/00* (2013.01)
USPC ............................ 205/413; 205/455; 205/464

(58) Field of Classification Search
USPC ......... 205/440, 443, 446, 448, 450, 455, 456, 205/462, 555, 413, 464
See application file for complete search history.

(56) References Cited

U.S. PATENT DOCUMENTS 1,280,622 A 10/1918 Andrews
1,962,140 A 6/1934 Dreyfus
(Continued)

FOREIGN PATENT DOCUMENTS

CA 1146120 A1 5/1983
CA 1272161 A1 7/1990
(Continued)

OTHER PUBLICATIONS

Kaneco et al., "Electrochemical Reduction of Carbon Dioxide to Ethylene with High Faradaic Efficiency at a Cu Electrode in CsOH/Methanol", Electrochimica Acta (no month, 1999), vol. 44, pp. 4701-4706.*

(Continued)

*Primary Examiner* — Edna Wong
(74) *Attorney, Agent, or Firm* — Suiter Swantz pc llo (57) ABSTRACT

The present disclosure is a system and method for producing a first product from a first region of an electrochemical cell having a cathode and a second product from a second region of the electrochemical cell having an anode. The method may include the step of contacting the first region of the electrochemical cell with a catholyte comprising an alcohol and carbon dioxide. Another step of the method may include contacting the second region of the electrochemical cell with an anolyte comprising the alcohol. Further, the method may include a step of applying an electrical potential between the anode and the cathode sufficient to produce a first product recoverable from the first region and a second product recoverable from the second region.

24 Claims, 7 Drawing Sheets

Related U.S. Application Data filed on Oct. 31, 2012, provisional application No. 61/703,158, filed on Sep. 19, 2012, provisional application No. 61/675,938, filed on Jul. 26, 2012, provisional application No. 61/703,229, filed on Sep. 19, 2012, provisional application No. 61/703,231, filed on Sep. 19, 2012, provisional application No. 61/703,232, filed on Sep. 19, 2012, provisional application No. 61/703,234, filed on Sep. 19, 2012, provisional application No. 61/703,238, filed on Sep. 19, 2012, provisional application No. 61/703,187, filed on Sep. 19, 2012.

(56) References Cited

U.S. PATENT DOCUMENTS

| | | |
|---|---|---|
| 3,019,256 A | 1/1962 | Dunn |
| 3,088,990 A | 5/1963 | Rightmire et al. |
| 3,293,292 A | 12/1966 | Olivier et al. |
| 3,326,998 A | 6/1967 | Reusser et al. |
| 3,341,615 A | 9/1967 | Wulf et al. |
| 3,341,616 A | 9/1967 | Vives |
| 3,344,046 A | 9/1967 | Neikam |
| 3,347,758 A | 10/1967 | Koehl, Jr. |
| 3,352,935 A | 11/1967 | Mahan |
| 3,361,653 A | 1/1968 | Miller |
| 3,401,100 A | 9/1968 | Macklin |
| 3,492,209 A | 1/1970 | Miller |
| 3,560,354 A | 2/1971 | Young |
| 3,607,962 A | 9/1971 | Krekeler et al. |
| 3,636,159 A | 1/1972 | Solomon |
| 3,720,591 A | 3/1973 | Skarlos |
| 3,745,180 A | 7/1973 | Rennie |
| 3,764,492 A | 10/1973 | Baizer et al. |
| 3,779,875 A | 12/1973 | Michelet |
| 3,894,059 A | 7/1975 | Selvaratnam |
| 3,959,094 A | 5/1976 | Steinberg |
| 4,072,583 A | 2/1978 | Hallcher et al. |
| 4,087,470 A | 5/1978 | Suzuki |
| 4,088,682 A | 5/1978 | Jordan |
| 4,147,599 A | 4/1979 | O'Leary et al. |
| 4,162,948 A | 7/1979 | Yagii et al. |
| 4,219,392 A | 8/1980 | Halmann |
| 4,245,114 A | 1/1981 | Peltzman |
| 4,253,921 A | 3/1981 | Baldwin et al. |
| 4,256,550 A | 3/1981 | Niinobe et al. |
| 4,267,070 A | 5/1981 | Nefedov et al. |
| 4,299,981 A | 11/1981 | Leonard |
| 4,343,690 A | 8/1982 | De Nora |
| 4,381,978 A | 5/1983 | Gratzel et al. |
| 4,421,613 A | 12/1983 | Goodridge et al. |
| 4,450,055 A | 5/1984 | Stafford |
| 4,476,003 A | 10/1984 | Frank et al. |
| 4,510,214 A | 4/1985 | Crouse et al. |
| 4,523,981 A | 6/1985 | Ang et al. |
| 4,545,886 A | 10/1985 | De Nora et al. |
| 4,547,271 A | 10/1985 | Bharucha et al. |
| 4,560,451 A | 12/1985 | Nielsen |
| 4,563,254 A | 1/1986 | Morduchowitz et al. |
| 4,595,465 A | 6/1986 | Ang et al. |
| 4,608,132 A | 8/1986 | Sammells |
| 4,608,133 A | 8/1986 | Morduchowitz et al. |
| 4,619,743 A | 10/1986 | Cook |
| 4,661,422 A | 4/1987 | Marianowski et al. |
| 4,673,473 A | 6/1987 | Ang et al. |
| 4,702,973 A | 10/1987 | Marianowski |
| 4,732,655 A | 3/1988 | Morduchowitz et al. |
| 4,756,807 A | 7/1988 | Meyer et al. |
| 4,845,252 A | 7/1989 | Schmidt et al. |
| 4,902,828 A | 2/1990 | Wickenhaeuser et al. |
| 4,968,393 A | 11/1990 | Mazur et al. |
| 5,074,974 A | 12/1991 | Toomey, Jr. |
| 5,084,148 A | 1/1992 | Kazcur et al. |
| 5,107,040 A | 4/1992 | Repman et al. |
| 5,155,256 A | 10/1992 | Chapman |
| 5,198,086 A | 3/1993 | Chlanda et al. |
| 5,246,551 A | 9/1993 | Pletcher et al. |
| 5,290,404 A | 3/1994 | Toomey et al. |
| 5,294,319 A | 3/1994 | Kaczur et al. |
| 5,300,369 A | 4/1994 | Dietrich et al. |
| 5,412,150 A | 5/1995 | Wessel |
| 5,443,804 A | 8/1995 | Parker et al. |
| 5,455,372 A | 10/1995 | Hirai et al. |
| 5,474,658 A | 12/1995 | Scharbert et al. |
| 5,514,492 A | 5/1996 | Marincic et al. |
| 5,536,856 A | 7/1996 | Harrison et al. |
| 5,654,493 A | 8/1997 | Wessel |
| 5,804,045 A | 9/1998 | Orillon et al. |
| 6,001,500 A | 12/1999 | Bass et al. |
| 6,024,935 A | 2/2000 | Mills et al. |
| 6,137,005 A | 10/2000 | Honevik |
| 6,171,551 B1 | 1/2001 | Malchesky et al. |
| 6,251,256 B1 | 6/2001 | Blay et al. |
| 6,312,655 B1 | 11/2001 | Hesse et al. |
| 6,348,613 B2 | 2/2002 | Miyamoto et al. |
| 6,380,446 B1 | 4/2002 | Drew et al. |
| 6,465,699 B1 | 10/2002 | Grosso |
| 6,492,047 B1 | 12/2002 | Peled et al. |
| 6,777,571 B2 | 8/2004 | Chaturvedi et al. |
| 6,881,320 B1 | 4/2005 | Krafton et al. |
| 6,949,178 B2 | 9/2005 | Tennakoon et al. |
| 7,138,201 B2 | 11/2006 | Inoue et al. |
| 7,462,752 B2 | 12/2008 | Fong et al. |
| 7,883,610 B2 | 2/2011 | Monzyk et al. |
| 8,227,127 B2 | 7/2012 | Little et al. |
| 8,277,631 B2 | 10/2012 | Eastman et al. |
| 8,313,634 B2 | 11/2012 | Bocarsly et al. |
| 8,444,844 B1 | 5/2013 | Teamey et al. |
| 8,562,811 B2 | 10/2013 | Sivasankar et al. |
| 8,663,447 B2 | 3/2014 | Bocarsly et al. |
| 2001/0026884 A1 | 10/2001 | Appleby et al. |
| 2002/0022753 A1 | 2/2002 | Drew et al. |
| 2004/0115489 A1 | 6/2004 | Goel |
| 2005/0139486 A1 | 6/2005 | Carson et al. |
| 2006/0102468 A1 | 5/2006 | Monzyk et al. |
| 2006/0269813 A1 | 11/2006 | Seabaugh et al. |
| 2007/0004023 A1 | 1/2007 | Trachtenberg |
| 2007/0012577 A1 | 1/2007 | Bulan et al. |
| 2007/0224479 A1 | 9/2007 | Tadokoro et al. |
| 2008/0223727 A1 | 9/2008 | Oloman et al. |
| 2008/0248350 A1 | 10/2008 | Little et al. |
| 2008/0283411 A1 | 11/2008 | Eastman et al. |
| 2008/0286643 A1 | 11/2008 | Iwasaki |
| 2008/0296146 A1 | 12/2008 | Toulhoat et al. |
| 2008/0314758 A1 | 12/2008 | Grosso |
| 2009/0014336 A1 | 1/2009 | Olah et al. |
| 2009/0030240 A1 | 1/2009 | Olah et al. |
| 2009/0057161 A1 | 3/2009 | Aulich et al. |
| 2009/0062110 A1 | 3/2009 | Koshino et al. |
| 2009/0308759 A1 | 12/2009 | Waycuilis |
| 2010/0069600 A1 | 3/2010 | Morelle et al. |
| 2010/0187123 A1 | 7/2010 | Bocarsly et al. |
| 2010/0187125 A1 | 7/2010 | Sandoval et al. |
| 2010/0191024 A1 | 7/2010 | Uenveren et al. |
| 2010/0196800 A1 | 8/2010 | Markoski et al. |
| 2010/0248042 A1 | 9/2010 | Nakagawa et al. |
| 2010/0270167 A1 | 10/2010 | McFarland |
| 2010/0282614 A1 | 11/2010 | Detournay et al. |
| 2010/0305629 A1 | 12/2010 | Lund et al. |
| 2010/0330435 A1 | 12/2010 | Nemeth et al. |
| 2011/0024288 A1 | 2/2011 | Bhavaraju et al. |
| 2011/0083968 A1 | 4/2011 | Gillliam et al. |
| 2011/0114501 A1 | 5/2011 | Teamey et al. |
| 2011/0114502 A1 | 5/2011 | Cole et al. |
| 2011/0114503 A1 | 5/2011 | Sivasankar et al. |
| 2011/0114504 A1 | 5/2011 | Sivasankar et al. |
| 2011/0143929 A1 | 6/2011 | Sato et al. |
| 2011/0177398 A1 | 7/2011 | Affinito et al. |
| 2011/0186441 A1 | 8/2011 | LaFrancois et al. |
| 2011/0226632 A1 | 9/2011 | Cole et al. |
| 2011/0237830 A1 | 9/2011 | Masel |
| 2011/0318617 A1 | 12/2011 | Kirchev et al. |
| 2012/0004448 A1 | 1/2012 | Bhattacharyya |
| 2012/0004449 A1 | 1/2012 | Bhattacharyya |

(56) References Cited

U.S. PATENT DOCUMENTS

| | | |
|---|---|---|
| 2012/0004454 A1 | 1/2012 | Bhattacharyya |
| 2012/0018311 A1 | 1/2012 | Yotsuhashi et al. |
| 2012/0043301 A1 | 2/2012 | Arvin et al. |
| 2012/0132537 A1 | 5/2012 | Sivasankar et al. |
| 2012/0132538 A1 | 5/2012 | Cole et al. |
| 2012/0199493 A1 | 8/2012 | Krafft et al. |
| 2012/0215034 A1 | 8/2012 | McFarland |
| 2012/0228147 A1 | 9/2012 | Sivasankar et al. |
| 2012/0277465 A1 | 11/2012 | Cole et al. |
| 2012/0292196 A1 | 11/2012 | Albrecht et al. |
| 2012/0295172 A1 | 11/2012 | Peled et al. |
| 2012/0298522 A1 | 11/2012 | Shipchandler et al. |
| 2012/0329657 A1 | 12/2012 | Eastman et al. |
| 2013/0062216 A1 | 3/2013 | Yotsuhashi et al. |
| 2013/0098772 A1 | 4/2013 | Bocarsly et al. |
| 2013/0105304 A1 | 5/2013 | Kaczur et al. |
| 2013/0105330 A1 | 5/2013 | Teamey et al. |
| 2013/0118907 A1 | 5/2013 | Deguchi et al. |
| 2013/0118911 A1 | 5/2013 | Sivasankar et al. |
| 2013/0134048 A1 | 5/2013 | Teamey et al. |
| 2013/0134049 A1 | 5/2013 | Teamey et al. |
| 2013/0140187 A1 | 6/2013 | Teamey et al. |
| 2013/0180863 A1 | 7/2013 | Kaczur et al. |
| 2013/0180865 A1 | 7/2013 | Cole et al. |
| 2013/0186771 A1 | 7/2013 | Zhai et al. |
| 2013/0199937 A1 | 8/2013 | Cole et al. |

FOREIGN PATENT DOCUMENTS

| | | | |
|---|---|---|---|
| CA | 2043256 A1 | 12/1991 | |
| CA | 2391938 A1 | 5/2001 | |
| CN | 102190573 A * | 9/2011 | ............ C07C 53/02 |
| DE | 1047765 A | 12/1958 | |
| DE | 2301032 A | 7/1974 | |
| EP | 0028430 A1 | 5/1981 | |
| EP | 2329875 A1 | 6/2011 | |
| FR | 853643 | 3/1940 | |
| GB | 1096847 A | 12/1967 | |
| GB | 1285209 A | 8/1972 | |
| GB | 1584524 A | 4/1977 | |
| GB | 2038335 A | 7/1980 | |
| GB | 2312218 A | 10/1997 | |
| JP | 64-015388 | 1/1989 | |
| WO | 91/01947 A1 | 2/1991 | |
| WO | WO 9724320 A1 | 7/1997 | |
| WO | 9850974 A1 | 11/1998 | |
| WO | WO 0015586 A1 | 3/2000 | |
| WO | WO0138275 A1 | 5/2001 | |
| WO | WO 2004067673 A1 | 8/2004 | |
| WO | 2006074335 A2 | 7/2006 | |
| WO | 2007041872 A1 | 4/2007 | |
| WO | WO 2007041872 A1 | 4/2007 | |
| WO | 2007/091616 A1 | 8/2007 | |
| WO | 2009108327 A1 | 9/2009 | |
| WO | 2011069008 | 6/2011 | |
| WO | 2011116236 A2 | 9/2011 | |
| WO | 2011160577 A1 | 12/2011 | |
| WO | 2012015921 A1 | 2/2012 | |
| WO | WO 2012046362 A1 | 4/2012 | |
| WO | 2012166997 A2 | 12/2012 | |

OTHER PUBLICATIONS

Yuan et al., "Electrochemical Activation of Carbon Dioxide for Synthesis of Dimethyl Carbonate in an Ionic Liquid", Electrochimica Acta (no month, 2009), vol. 54, pp. 2912-2915.*

Kaneco et al., "Electrochemical Conversion of Carbon Dioxide to Formic Acid on Pb in KOH/Methanol Electrolyte at Ambient Temperature and Pressure", Energy (no month, 1998), vol. 23, No. 12, pp. 1107-1112.*

Seshardi G., Lin C., Bocarsly A.B., A new homogeneous electrocatalyst for the reduction of carbon dioxide to methanol at low overpotential, Journal of Electroanalytical Chemistry, 1994, 372, pp. 145-150.

Eggins, Brown, McNeill, and Grimshaw, Carbon Dioxide Fixation by Electrochemical Reduction in Water to Oxalate and Glyoxylate, Tetrahedron Letters vol. 29, No. 8, pp. 945-948, 1988, Pergamon Journals Ltd., Printed in Great Britain.

M. Alvarez-Guerra et al., Conversion of carbon dioxide into formate using a continuous electrochemical reduction process in a lead cathode, Chem. Eng. J. (2012), http://dx.doi.org/10.1016/j.cej.2012.06.099.

Satoshi Kaneco, Kenji Iiba, Nobu-Hide Hiei, Kiyohisa Ohta, Takayuki Mizuno, and Tohru Suzuki, Electrochemical reduction of carbon dioxide to ethylene with high Faradaic efficiency at a Cu electrode in CsOH/methanol, Electrochimica Acta 44 (1999) 47001-4706.

Keith Scott, A Preliminary Investigation of the Simultaneous Anodic and Cathodic Production of Glyoxylic Acid, Electrochimica Acta, vol. 36, No. 9, pp. 1447-1452, 1991, Printed in Great Britain.

B. Eneau-Innocent et al., Electroreduction of carbon dioxide at a lead electrode in propylene carbonate: A spectroscopic study, Applied Catalysis B: Environmental 98 (2010) 65-71.

Kotaro Ogura et al., Selective Conversion of CO2 to Ethylene by the Electrolysis at a Three-Phase (Gas/Liquid/Solid) Interface in an Acidic Solution Containing Cupric Ions, Fuel Chemistry Division Preprints 2003, 48(1), 264.

S. Gambino and G. Silvestri, On the electrochemical reduction of carbon dioxide and ethylene, Tetrahedron Letters No. 32, pp. 3025-3028, 1973, Pergamon Press, Printed in Great Britain.

K.S. Udupa, G.S. Subramanian, and H.V.L. Udupa, The electrolytic reduction of carbon dioxide to formic acid, Electrochimica Acta, 1971, vol. 16, pp. 1593-1598, Pergamon Press, Printed in Northern Ireland.

Green et al., "Vapor-Liquid Equilibria of Formaldehyde-Methanol-Water", Industrial and Engineering Chemistry (Jan. 1955), vol. 47, No. 1, pp. 103-109.

Shibata et al., "Electrochemical Synthesis of Urea at Gas-Diffusion Electrodes Part VI. Simultaneous Reduction of Carbon Dioxide and Nitrite Ions with Various Metallophthalocyanine Catalysts". J. of Electroanalytical Chemistry (no month, 2001), vol. 507, pp. 177-184.

Jaaskelainen and Haukka, The Use of Carbon Dioxide in Ruthenium Carbonyl Catalyzed 1-hexene Hydroformylation Promoted by Alkali Metal and Alkaline Earth Salts, Applied Catalysis A: General, 247, 95-100 (2003).

Heldebrant et al., "Reversible Zwitterionic Liquids, The Reaction of Alkanol Guanidines, Alkanol Amidines, and Diamines with CO2", Green Chem. (mo month, 2010), vol. 12, pp. 713-721.

Perez et al., "Activation of Carbon Dioxide by Bicyclic Amidines", J. Org. Chem. (no month, 2004), vol. 69, pp. 8005-8011.

Seshadri et al., A New Homogeneous Electrocatalyst for the Reduction of Carbon Dioxide to Methanol at Low Overpotential, Journal of Electroanalytical Chemistry, 372 (1994), 145-50.

Green, et al., Vapor-Liquid Equilibria of Formaldehyde-Methanol-Water, Industrial and Engineering Chemistry (Jan. 1955), vol. 47, No. 1, pp. 103-109.

Scibioh et al., Electrochemical Reduction of Carbon Dioxide: A Status Report, Proc Indian Natn Sci Acad (May 2004), vol. 70, A, No. 3, pp. 407-462.

Gennaro et al., Homogeneous Electron Transfer Catalysis of the Electrochemical Reduction of Carbon Dioxide. Do Aromatic Anion Radicals in an Outer-Sphere Manner?, J. Am. Chem. Soc. (no month, 1996), vol. 118, pp. 7190-7196.

Perez et al., Activation of Carbon Dioxide by Bicyclic Amidines, J. Org. Chem. (no month, 2004), vol. 69, pp. 8005-8011.

Zaragoza Dorwald, Side Reactions in Organic Synthesis, 2005, Wiley-VCH Verlag GmbH & Co. KGaA, Weinheim, Preface. Pg. IX.

Liansheng et al, Journal of South Central University Technology, Electrode Selection of Electrolysis with Membrane for Sodium Tungstate Solution, 1999, 6(2), pp. 107-110.

Mahmood et al., Use of Gas-Diffusion Electrodes for High-Rate Electrochemical Reduction of Carbon Dioxide. II. Reduction at Metal Phthalocyanine-Impregnated Electrodes, J. of Appl. Electrochem. (no month, 1987), vol. 17, pp. 1223-1227.

Tanno et al., Electrolysis of Iodine Solution in a New Sodium Bicarbonate-Iodine Hybrid Cycle, International Journal of Hydrogen Energy (no month, 1984), vol. 9, No. 10, pp. 841-848.

(56) References Cited

OTHER PUBLICATIONS

Hori et al, chapter on "Electrochemical CO2 Reduction on Metal Electrodes," in the book "Modern Aspects of Electrochemistry," vol. 42, pp. 106 and 107.
Czerwinski et al, "Adsorption Study of CO2 on Reticulated vitreous carbon (RVC) covered with platinum," Analytical Letters, vol. 18, Issue 14 (1985), pp. 1717-1722.
Hammouche et al, Chemical Catalysis of Electrochemical Reactions. Homogeneous Catalysis of the Electrochemical Reduction of Carbon Dioxide by Iron ("0") Porphyrins. Role of the Addition of Magnesium Cations. J. Am. Chem. Soc. 1991, 113, 8455-8466.
Hossain et al., Palladium and Cobalt Complexes of Substituted Quinoline, Bipyridine and Phenanthroline as Catalysts for Electrochemical Reduction of Carbon Dioxide, Electrochimica Acta (no month, 1997), vol. 42, No. 16, pp. 2577-2785.
Scibioh et al., "Electrochemical Reduction of Carbon Dioxide: A Status Report", Proc Indian Natn Sci Acad (May 2004), vol. 70, A, No. 3, pp. 407-462.
Seshadri et al., "A new homogeneous electrocatalyst for the reduction of carbon dioxide to methanol at low overpotential", Journal of Electroanalytical Chemistry and Interfacial Electro Chemistry, Elsevier, Amsterdam, NL, vol. 372, No. 1-2, Jul. 8, 1994, pp. 145-150.
Hossain et al., "Palladium and cobalt complexes of substituted quinoline, bipyridine and phenanthroline as catalysts for electrochemical reduction of carbon dioxide", Electrochimica Acta, Elsevier Science Publishers, vol. 42, No. 16, Jan. 1, 1997, pp. 2577-2585.
Fisher et al., "Electrocatalytic reduction of carbon dioxide by using macrocycles of nickel and cobalt", Journal of the American Chemical Society, vol. 102, No. 24, Sep. 1, 1980, pp. 7361-7363.
Ishida et al., Selective Formation of HC00—In the Electrochemical CO2 Reduction Catalyzed by URU(BPY)2(CO)2 3/4 2+ (BPY = 2,2'-Bipyridine), Journal of the Chemical Society, Chemical Communications, Chemical Society, Letchworth, GB, Jan. 1, 1987, pp. 131-132.
Zhao et al., "Electrochemical reduction of supercritical carbon dioxide in ionic liquid 1-n-butyl-3-methylimidazolium hexafluorophosphate", Journal of Supercritical Fluids, PRA Press, US, vol. 32, No. 1-3, Dec. 1, 2004, pp. 287-291.
Scibioh et al, "Electrochemical Reductin of Carbon Dioxide: A Status Report," Proc. Indian Natn Science Acad., 70, A, No. 3, May 2004, pp. 407-762.
Fukaya et al., "Electrochemical Reduction of Carbon Dioxide to Formate Catalyzed by Rh(bpy)3CI3", Kagaku Gijutsu Kenkyusho Hokoku (no month, 1986), vol. 81, No. 5, pp. 255-258. 1-page abstract only.
Li et al., "the Electro-Reduction of Carbon Dioxide in a Continuous Reactor", J. of Applied Electrochemistry (no month, 2005), vol. 35, pp. 955-965.
U.S. Appl. No. 13/724,647, filed Dec. 21, 2012; Office Action mailed Oct. 17, 2013.
U.S. Appl. No. 13/787,481, filed Mar. 6, 2013; Office Action mailed Sep. 13, 2013.
U.S. Appl. No. 13/724,082, filed Dec. 21, 2012; Office Action mailed Aug. 12, 2013.
U.S. Appl. No. 13/724,522, filed Dec. 21, 2012; Office Action mailed Oct. 1, 2013.
U.S. Appl. No. 13/724,885, filed Dec. 21, 2012; Office Action mailed Aug. 21, 2013.
U.S. Appl. No. 13/724,231, filed Dec. 21, 2012; Office Action mailed Aug. 20, 2013.
Wu et al., "Electrochemical Reduction of Carbon Dioxide I. Effects of the Electrolyte on the Selectivity and Activity with Sn Electrode", Journal of the Electrochemical Society (no month, 2012), vol. 159, No. 7, pp. F353-F359.
Chaplin et al., "Effects of Process Conditions and Electrode Material on Reaction Pathways for Carbon Dioxide Electroreduction with Particular Reference to Formate Formation", Journal of Applied Electrochemistry (no month, 2003), vol. 33, pp. 1107-1123.
Jaime-Ferrer et al., "Three-Compartment Bipolar Membrane Electrodialysis for Splitting of Sodium Formate into Formic Acid and Sodium Hydroxide: Role of Diffusion of Molecular Acid", Journal of Membrane Science (no month, 2008), vol. 325, pp. 528-536.
James, Grimshaw, Electrochemical Reactions and Mechanisms in Organic Chemistry, 2000, ISBN 978-0-444-72007-8. [retrieved on Jan. 3, 2014]. Retrieved from the internet. <URL: http://f3.tiera.ru/ShiZ/Great%20Science%20TextBooks/Great%Science%20Textbooks%20DVD%20Library%202007%20-%20Supplement%20Five/Chemistry/Organic%20Chemistry/Electrochemical%20Reactions%20and%20Mechanisms%20in%20Organic%20Chemistry%20-%20J.%20Grimshaw%20%28Elsevier,%202000%29%WW.pdf>.
Fischer, J. et al. "The production of oxalic acid from CO2 and H2O." Journal of Applied Electrochemistry, 1981, vol. 11, pp. 743-750.
Goodridge, F. et al., The electrolytic reduction of carbon dioxide and monoxide for the production of carboxylic acids.: Journal of applied electrochemistry, 1984, vol. 14, pp. 791-796.
Chen et al., "Tin oxide dependence of the CO2 reduction efficiency on tin electrodes and enhanced activity for tin/tin oxide thin-film catalysts." Journal of the American Chemical Society 134, No. 4 (2012): 1986-1989, Jan. 9, 2012, retrieved on-line.
Zhou et al. "Anodic passivation processes of indium in alkaline solution [J]" Journal of Chinese Society for Corrosion and Protection 1 (2005): 005, Feb. 2005.
Fukaya et al., "Electrochemical Reduction of Carbon Dioxide to Formate Catalyzed by Rh(bpy)3CI3", Kagaku Gijutsu Kenkyusho Hokoku (no month, 1986), vol. 81, No. 5, pp. 255-258.
Seshadri et al, "A new homogeneous catalyst for the reduction of carbon dioxide to methanol at low overpotential," Journal of Electroanalytical Chemistry, 372 (1994) 145-150.
Scibioh et al, "Electrochemical Reduction of Carbon Dioxide: A Status Report," Proc. Indian Natn Science Acad., 70, A, No. 3, May 2004, pp. 407-762.
Hori et al, "Enhanced Formation of Ethylene and Alcohols at Ambient Temperature and Pressure in Electrochemical Reduction of Carbon Dioxide at a Copper Electrode," J. Chem. Soc. Chem. Commun. (1988), pp. 17-19.
Hossain et al, "Palladium and Cobalt Complexes of Substituted Quinoline, Bipyridine and Phenanthroline as Catalysts for Electrochemical Reduction of Carbon Dioxide," Electrochimica Acta, vol. 42, No. 16 (1997), pp. 2577-2585.
Fischer, "Liquid Fuels from Water Gas", Industrial and Engineering Chemistry, vol. 17, No. 6, Jun. 1925, pp. 574-576.
Williamson et al, "Rate of Absorption and Equilibrium of Carbon Dioxide in Alkaline Solutions", Industrial and Engineering Chemistry, vol. 16, No. 11, Nov. 1924, pp. 1157-1161.
Hori, "Electrochemical CO2 Reduction on Metal Electrodes", Modern Aspects of Electrochemistry, No. 42, 2008, pp. 89-189.
Nefedov and Manov-Yuvenskii, The Effect of Pyridine Bases and Transition-Metal Oxides on the Activity of PdCl2 in the Carbonylation of Aromatic Mononitro Compounds by Carbon Monoxide, 28 Bulletin of the Acad. of Sciences of the USSR 3, 540-543 (1979).
Vojinovic "Bromine oxidation and bromine reduction in propylene carbonate" Journal of Electroanalytical Chemistry, 547 (2003) pp. 109-113.
Babic et al (Electrochimica Acta, 51, 2006, 3820-3826).
Yoshida et al. (Journal of Electroanalytical Chemistry, 385, 1995, 209-225).

\* cited by examiner

ELECTROCHEMICAL REDUCTION OF CO₂ WITH CO-OXIDATION OF AN ALCOHOL

CROSS-REFERENCE TO RELATED APPLICATIONS

The present application claims the benefit under 35 U.S.C. §119(e) of U.S. Provisional Application Ser. No. 61/720,670 filed Oct. 31, 2012, U.S. Provisional Application Ser. No. 61/703,175 filed Sep. 19, 2012 and U.S. Provisional Application Ser. No. 61/675,938 filed Jul. 26, 2012. Said U.S. Provisional Application Ser. No. 61/720,670 filed Oct. 31, 2012, U.S. Provisional Application Ser. No. 61/703,175 filed Sep. 19, 2012 and U.S. Provisional Application Ser. No. 61/675,938 filed Jul. 26, 2012 are incorporated by reference in their entireties.

The present application also claims the benefit under 35 U.S.C. §119(e) of U.S. Provisional Application Ser. No. 61/703,229 filed Sep. 19, 2012, U.S. Provisional Application Ser. No. 61/703,158 filed Sep. 19, 2012, U.S. Provisional Application Ser. No. 61/703,231 filed Sep. 19, 2012, U.S. Provisional Application Ser. No. 61/703,232, filed Sep. 19, 2012, U.S. Provisional Application Ser. No. 61/703,234, filed Sep. 19, 2012, U.S. Provisional Application Ser. No. 61/703,238 filed Sep. 19, 2012, U.S. Provisional Application Ser. No. 61/703,187 filed Sep. 19, 2012. The U.S. Provisional Application Ser. No. 61/703,229 filed Sep. 19, 2012, U.S. Provisional Application Ser. No. 61/703,158 filed Sep. 19, 2012, U.S. Provisional Application Ser. No. 61/703,231 filed Sep. 19, 2012, U.S. Provisional Application Ser. No. 61/703,232, filed Sep. 19, 2012, United States Provisional Application Ser. No. 61/703,234, filed Sep. 19, 2012, U.S. Provisional Application Ser. No. 61/703,238 filed Sep. 19, 2012 and U.S. Provisional Application Ser. No. 61/703,187 filed Sep. 19, 2012 are hereby incorporated by reference in their entireties.

CROSS REFERENCE TO RELATED APPLICATIONS

The present application incorporates by reference co-pending U.S. patent application Ser. No. 13/724,339 filed on Dec. 21, 2012, U.S. patent application Ser. No. 13/724,878 filed on Dec. 21, 2012, U.S. patent application Ser. No. 13/724,647 filed on Dec. 21, 2012, U.S. patent application Ser. No. 13/724,807 filed on Dec. 21, 2012, U.S. patent application Ser. No. 13/724,996 filed on Dec. 21, 2012, U.S. patent application Ser. No. 13/724,719 filed on Dec. 21, 2012, U.S. patent application Ser. No. 13/724,082 filed on Dec. 21, 2012, and U.S. patent application Ser. No. 13/724,768 filed on Dec. 21, 2012, now U.S. Pat. No. 8,444,844 in their entireties.

TECHNICAL FIELD

The present disclosure generally relates to the field of electrochemical reactions, and more particularly to methods and/or systems for electrochemical reduction of carbon dioxide with co-oxidation of an alcohol.

BACKGROUND

The combustion of fossil fuels in activities such as electricity generation, transportation, and manufacturing produces billions of tons of carbon dioxide annually. Research since the 1970s indicates increasing concentrations of carbon dioxide in the atmosphere may be responsible for altering the Earth's climate, changing the pH of the ocean and other potentially damaging effects. Countries around the world, including the United States, are seeking ways to mitigate emissions of carbon dioxide.

A mechanism for mitigating emissions is to convert carbon dioxide into economically valuable materials such as fuels and industrial chemicals. If the carbon dioxide is converted using energy from renewable sources, both mitigation of carbon dioxide emissions and conversion of renewable energy into a chemical form that can be stored for later use will be possible.

SUMMARY

The present disclosure is directed to a system and method for producing a first product from a first region of an electrochemical cell having a cathode and a second product from a second region of the electrochemical cell having an anode. The method may include the step of contacting the first region of the electrochemical cell with a catholyte comprising carbon dioxide and optionally an alcohol. Another step of the method may include contacting the second region of the electrochemical cell with an anolyte comprising an alcohol. Further, the method may include a step of applying an electrical potential between the anode and the cathode sufficient to produce a first product recoverable from the first region and a second product recoverable from the second region.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

Referring generally to FIGS. 1-6, systems and methods of electrochemical co-production of products with a carbon-based reactant, such as an alcohol, supplied to an anode are disclosed. It is contemplated that the electrochemical co-production of products may include a production of a first product, such as reduction of carbon dioxide to carbon-based products to include one, two, three, and four carbon chemicals, at a cathode side of an electrochemical cell with coproduction of a second product, such as an oxidized carbon-based product, at the anode of the electrochemical cell whereby the anolyte includes an alcohol.

Before any embodiments of the disclosure are explained in detail, it is to be understood that the embodiments may not be limited in application according to the details of the structure or the function as set forth in the following descriptions or illustrated in the figures. Different embodiments may be capable of being practiced or carried out in various ways. Also, it is to be understood that the phraseology and terminology used herein is for the purpose of description and should not be regarded as limiting. The use of terms such as "including," "comprising," or "having" and variations thereof herein are generally meant to encompass the item listed thereafter and equivalents thereof as well as additional items. Further, unless otherwise noted, technical terms may be used according to conventional usage. It is further contemplated that like reference numbers may describe similar components and the equivalents thereof.

Figure 1A:
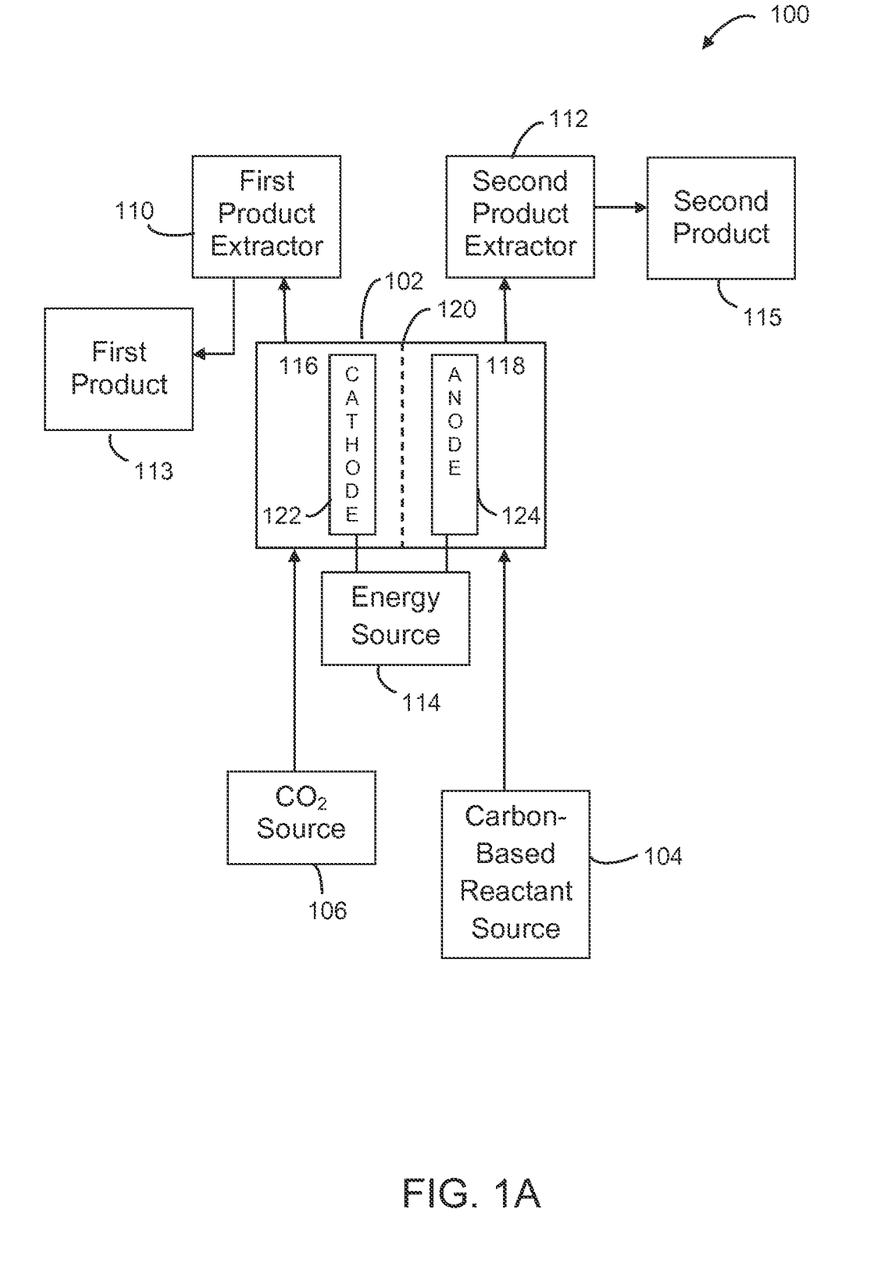
FIG. 1A is a block diagram of a system in accordance with an embodiment of the present disclosure.

Referring to FIG. 1A, a block diagram of a system 100 in accordance with an embodiment of the present disclosure is shown. System (or apparatus) 100 generally includes an electrochemical cell (also referred as a container, electrolyzer, or cell) 102, a carbon based reactant source 104, a carbon dioxide source 106, a first product extractor 110 and a first product 113, a second product extractor 112, second product 115, and an energy source 114.

Electrochemical cell 102 may be implemented as a divided cell. The divided cell may be a divided electrochemical cell and/or a divided photoelectrochemical cell. Electrochemical cell 102 may include a first region 116 and a second region 118. First region 116 and second region 118 may refer to a compartment, section, or generally enclosed space, and the like without departing from the scope and intent of the present disclosure. First region 116 may include a cathode 122. Second region 118 may include an anode 124. First region 116 may include a catholyte whereby carbon dioxide is dissolved in the catholyte. A heterocyclic catalyst, such as pyridine, imidazole, lutadines, or bipyridines, may also be in the catholyte. Second region 118 may include an anolyte which may include an alcohol. The anolyte may be free of halide ions. Energy source 114 may generate an electrical potential between the anode 124 and the cathode 122. The electrical potential may be a DC voltage. Energy source 114 may be configured to implement a variable voltage or variable current source. Separator 120 may selectively control a flow of ions between the first region 116 and the second region 118. Separator 120 may include an ion conducting membrane or diaphragm material.

Electrochemical cell 102 is generally operational to reduce carbon dioxide in the first region 116 to a first product 113 recoverable from the first region 116 while producing a second product 115 recoverable from the second region 118. Cathode 122 may reduce the carbon dioxide into a first product 113 that may include one or more compounds. Examples of the first product 113 recoverable from the first region 116 by first product extractor 110 may include carbon monoxide, formic acid, formaldehyde, methanol, oxalate, oxalic acid, glyoxylic acid, glycolic acid, glyoxal, glycolaldehyde, ethylene glycol, acetic acid, acetaldehyde, ethanol, ethylene, methane, ethane, lactic acid, propanoic acid, acetone, isopropanol, 1-propanol, 1,2-propylene glycol, propane, 1-butanol, and 2-butanol.

Carbon dioxide source 106 may provide carbon dioxide to the first region 116 of electrochemical cell 102. In some embodiments, the carbon dioxide is introduced directly into the region 116 containing the cathode 122.

First product extractor 110 may implement an organic product and/or inorganic product extractor. First product extractor 110 is generally operational to extract (separate) the first product 113 from the first region 116. The extracted first product 113 may be presented through a port of the system 100 for subsequent storage and/or consumption by other devices and/or processes.

Second product extractor 112 may extract the second product 115 from the second region 118. The extracted second product 115 may be presented through a port of the system 100 for subsequent storage and/or consumption by other devices and/or processes.

The anode side of the reaction occurring in the second region 118 may include a carbon-based reactant 104, such as an alcohol, which may be in the form of a gas phase, liquid phase, or as a mixed solution phase reactant supplied to the second region 118. The reaction occurring in the second region 118 may include a variety of oxidations such as the oxidation of a primary alcohol to an aldehyde or a secondary alcohol to a ketone. The second product recoverable from the second region 118 may also include a carboxylic acid, or both a carboxylic acid and an aldehyde. The carboxylic acid may include formic acid, acetic acid, propanoic acid, butanoic acid, or acrylic acid. Examples of the second product 115 recoverable from the second region 118 and the carbon-based reactant supplied to the second region 118 are in the table below.

TABLE 1

| Chemical Feed to Anode | Oxidation Product(s) |
| --- | --- |
| Methanol | Formaldehyde, Formic Acid |
| Ethanol | Acetaldehyde, Acetic Acid |
| Ethylene Glycol | Glycolaldehyde, Glyoxal, Glycolic Acid, Glyoxylic Acid, Oxalic Acid |
| Glycerol | Glyceraldehyde, dihydroxyacetone, 2,3 Dihydroxypropionic acid |
| Polyols | Polyol-aldehydes, Polyol-ketones, Polyol-carboxylic acids |
| 2-Propanol | 2-Propanone (Acetone) |
| 1-Propanol | Propionaldehyde, Propanoic Acid |
| 1-Butanol | Butyraldehyde, Butanoic Acid |
| 2-Butanol | Butanone |
| Phenol | Hydroquinone 1-2 dihydrobenzene (Catechol). 2,5 Cyclohexadiene-1-one Benzoquinone, Maleic Acid, Oxalic Acid |
| Benzyl Alcohol | Benzaldehyde, Benzoic Acid |
| Allyl Alcohol | Acrolein, Acrylic Acid |

Figure 1B:
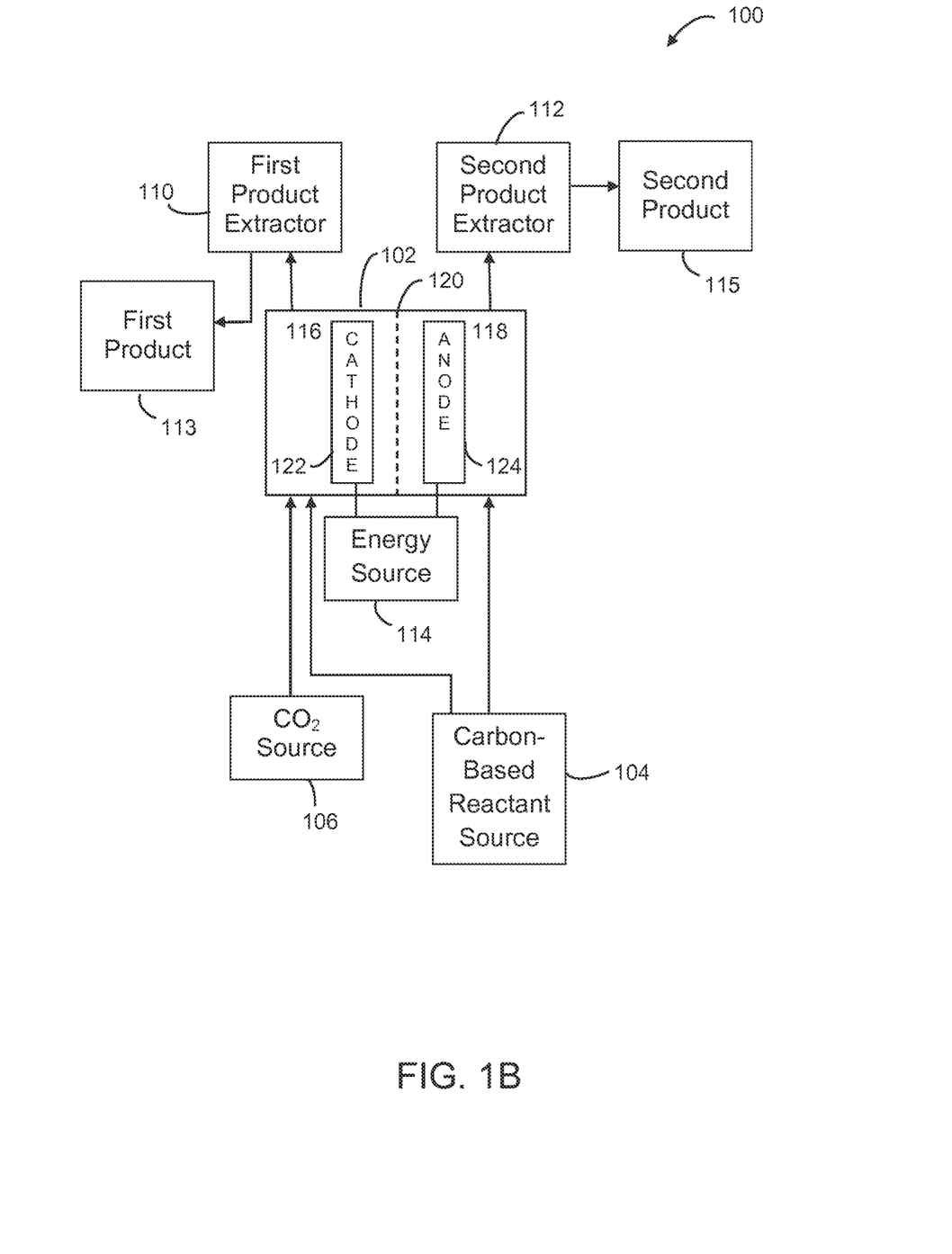
FIG. 1B is a block diagram of a system in accordance with an embodiment of the present disclosure.

In one embodiment shown in FIG. 1B, the cathode side of the reaction occurring in the first region 116 may also receive a feed of the alcohol. In this embodiment, the alcohol is supplied to the first region 116 in addition to the carbon dioxide source 106. The alcohol may act as a solvent for the carbon dioxide in the first region 116 and the alcohol and carbon dioxide source 106 may be supplied in a solution.

A glycol or diol or polyol may also serve as a solvent and reactant in the cell. For instance, ethylene glycol or glycerol might be a solvent in the electrochemical cell and cathode reactions involving the reduction of carbon dioxide or other carbon-based compounds would take place in the ethylene glycol or glycerol. At the anode, ethylene glycol would be oxidized to a product or products such as glyoxal or glyoxylic acid, and glycerol would be oxidized to a product or products such as glyceraldehyde, glyceric acid, glycolic acid, dihydroxyacetone, or 2,3 dihydroxypropionic acid. Other polyols could be used and would be oxidized to corresponding, polyol-aldehydes, polyol-ketones, and polyol-carboxylic acids.

Through the co-production of a first product 113 and a second product 115, the overall energy requirement for making each of the first product 113 and second product 115 may be reduced by 50% or more. In addition, electrochemical cell 102 may be capable of simultaneously producing two or more products with high selectivity.

Figure 2:
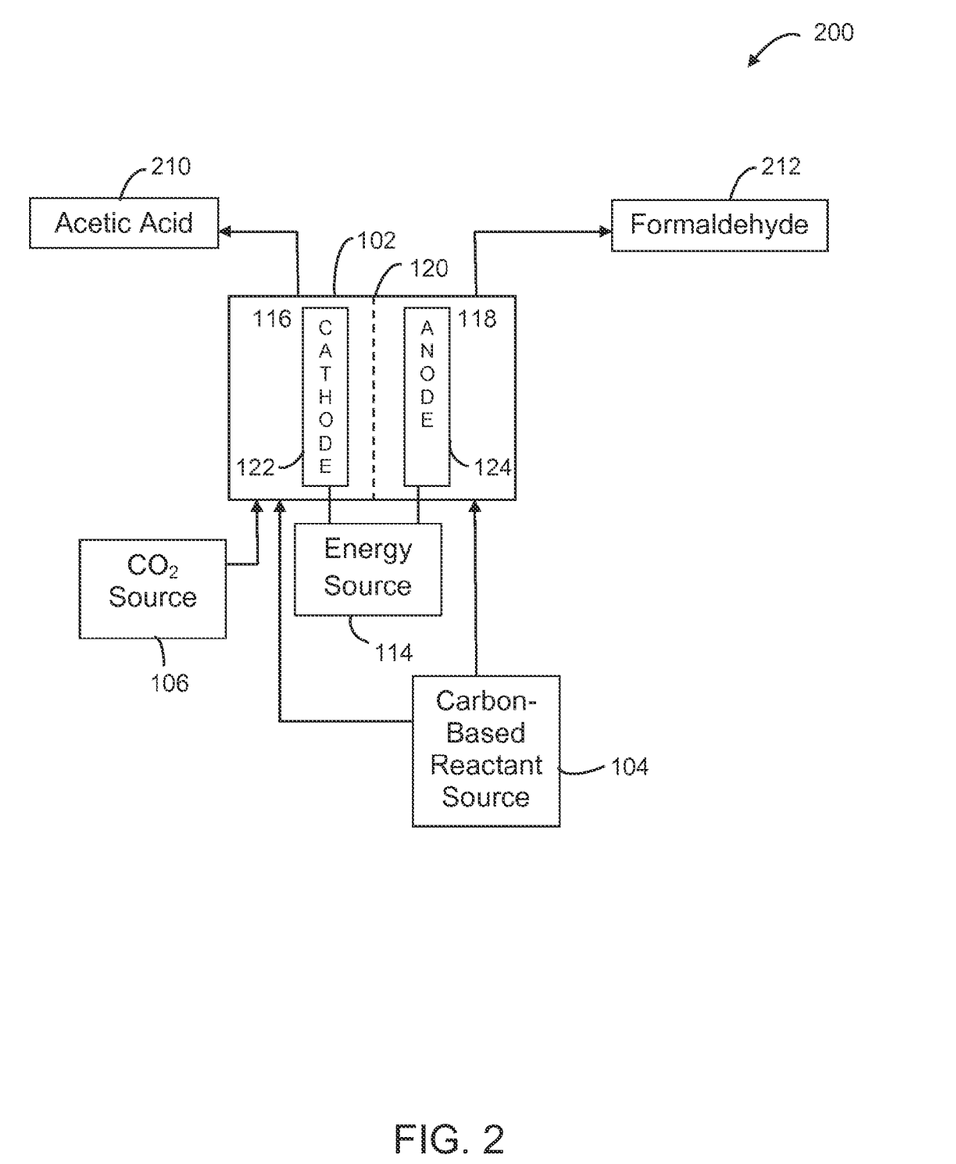
FIG. 2 is a block diagram of a system in accordance with another embodiment of the present disclosure.

A preferred embodiment of the present disclosure is the use of a methanol feed to both the anode and the cathode to make organic chemicals such as acetic acid at the cathode while simultaneously making formaldehyde at the anode. Referring to FIG. 2, system 200 for co-production of acetic acid 210 and formaldehyde 212 is shown. The oxidation of alcohol, such as methanol 220 in the second region 118 produces protons and electrons that are utilized to reduce carbon dioxide in the first region 116. The hydrogen resulting from the oxidation reaction at the second region 118 may be reacted with the carbon dioxide and the methanol provided by alcohol source 104 to the first region 116 to selectively produce acetate or acetic acid 210.

Formaldehyde 212 is produced at the second region 118 from $CO_2$ and the methanol provided by alcohol source 104. The alcohol source 104 is thus used both in the oxidation of the second product (formaldehyde 212) and in the transfer of hydrogen from the carbon-based reactant to the first region 116 for $CO_2$ reduction. The alcohol may serve as the primary hydrogen source for $CO_2$ reduction. Both the first region 116 and the second region 118 may utilize the methanol provided by alcohol source 104 as part of the catholyte or anolyte.

In one embodiment of the disclosure, when the first product is acetic acid 210 and the second product is formaldehyde 212 from methanol provided by alcohol source 104, then the molar ratio of the products may be 1 acetic acid:4 formaldehyde because acetic acid production from $CO_2$ is an 8 electron process and formaldehyde production from methanol is a two electron process. Specifically, the anode reaction is:

$$4CH_3OH => 4CH_2O + 8H^+ + 8e^-$$

In the anode reaction, methanol is provided by alcohol source 104 and the methanol is oxidized to formaldehyde, and 2 hydrogen ions are formed which pass through the separator/membrane separating the first region 116 from the second region 118.

The cathode reaction is the formation of acetate or acetic acid as follows:

$$2CO_2 + 8H^+ + 8e^- => CH_3COO^- + H^+ + 2H_2O$$

In the cathode reaction, hydrogen ions from the second region 118 pass through the membrane to the first region 116 to react with carbon dioxide to form acetic acid or acetate.

The combined reaction of methanol with carbon dioxide to form formaldehyde and acetic acid of the embodiment of the system shown in FIG. 2 is:

$$4CH_3OH + 2CO_2 => 4CH_2O + CH_3COO + H^+ + 2H_2O$$

The combined reaction for the production of formaldehyde from methanol oxidation may be controlled through selection of the anode material, anode material morphology, half-cell potential, the flow rate, and the concentration of water in the methanol feed, as well as other factors.

The concentration of the formaldehyde product leaving the second region may be from 1 to 50% by weight in one embodiment, and more preferably 10 to 40% by weight. The methanol concentration may determine the anolyte conductivity, and should be sufficient in concentration to maintain low voltages in the second region. Preferably, the concentration ranges from 1 to 100% and more preferably from 5 to 90%.

While system 200 of FIG. 2 is shown with a reactant of methanol, it is contemplated that other types of alcohols may be supplied by alcohol source 104 to produce various types of products (first product and second product) as desired and shown in an exemplary fashion in Table 1. It is further contemplated that other types of products may be co-produced by the anode and cathode of an electrochemical cell without departing from the scope and intent of the present disclosure.

Reactions occurring at the first region 116 may occur in a catholyte which may include water, methanol, ethanol, acetonitrile, propylene carbonate, ethylene carbonate, dimethyl carbonate, diethyl carbonate, dimethylsulfoxide, dimethylformamide, acetonitrile, acetone, tetrahydrofuran, N,N-dimethylacetamide, dimethoxyethane, diethylene glycol dimethyl ester, butyronitrile, 1,2-difluorobenzene, γ-butyrolactone, N-methyl-2-pyrrolidone, sulfolane, 1,4-dioxane, nitrobenzene, nitromethane, acetic anhydride, ionic liquids, or other catholytes in which $CO_2$ is soluble. The alcohol source 104 and carbon dioxide source 106 may be configured to supply the carbon-based reactant and carbon dioxide separately or jointly. The alcohol source 104 and carbon dioxide source 106 may be supplied in a solution. The carbon-based reactant source 104 and carbon dioxide source 106 may also be configured to supply the alcohol and carbon dioxide in solution with the catholyte.

The reactions occurring at the second region 118 may be in a gas phase, for instance in the case of gas phase reactants such as methane. The reaction at the second region 118 may also occur in liquid phase.

A catalyst may be employed in the second region 118 to promote the reaction. For example, a metal or metal oxide catalyst may be incorporated into the anode 124 in order to decrease the anode 124 potential and/or increase anode 124 current density, in addition to improving the selectivity of the oxidation reaction to the products desired. Examples of catalysts may include the metal and metal oxides of transition metals and their alloys and mixtures, including those of W, Mo, V, Fe, Ru, Ir, Au, and Pt. These catalysts may be deposited on the anode structure surfaces and/or on separate supports located in the second region on inorganic or carbon based supports. In addition, the catalyst may also consist of other forms or compositions suitable for the oxidation of the alcohols such as boron-doped diamond films deposited on conductive metal or inorganic supports.

Figure 3:
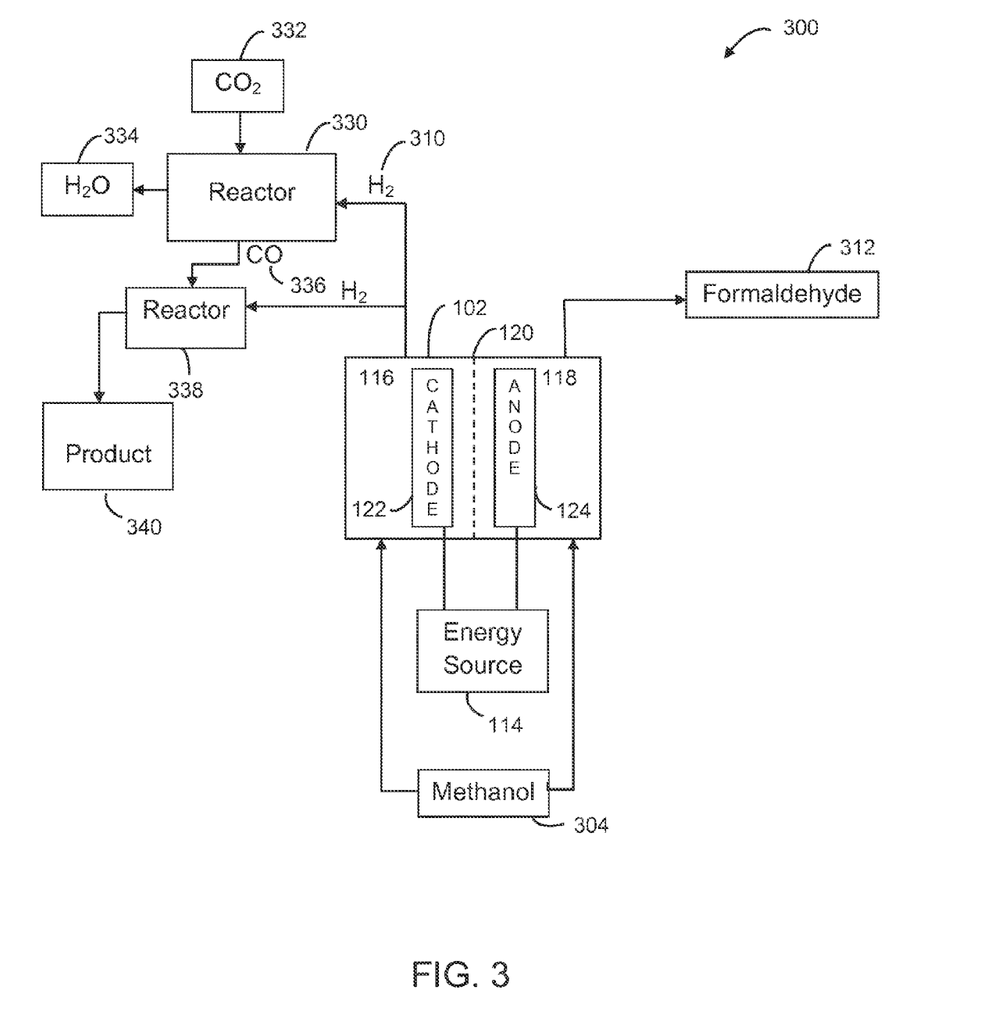
FIG. 3 is a block diagram of a system in accordance with an additional embodiment of the present disclosure.
Figure 4:
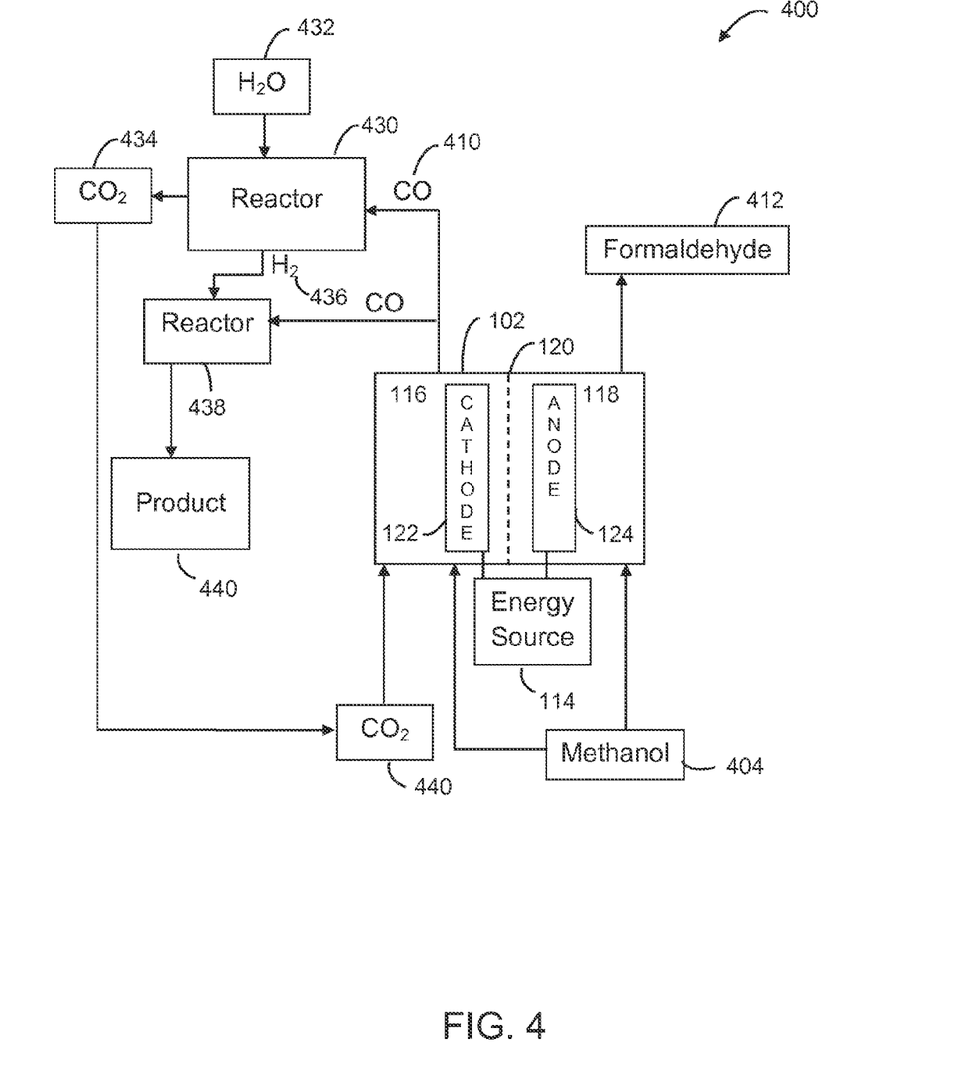
FIG. 4 is a block diagram of a system in accordance with another additional embodiment of the present disclosure.

Referring to FIGS. 3-4, block diagrams of systems 300, 400 in accordance with additional embodiments of the present disclosure are shown. Systems 300, 400 provide additional embodiments to systems 100, 200 of FIGS. 1A, 1B, and 2 to co-produce a first product and second product.

Referring to specifically to FIG. 3, first region 116 may produce a first product of $H_2$ 310 which is combined with carbon dioxide 332 in a reactor 330 which may perform a reverse water gas shift reaction. This reverse water gas shift reaction performed by reactor 330 may produce water 334 and carbon monoxide 336. Carbon monoxide 336 along with $H_2$ 310 may be combined at reactor 338. Reactor 338 may cause a reaction, such as a Fischer-Tropsch synthesis, to reduce carbon monoxide to a product 340. Product 340 may include methane, methanol, hydrocarbons, glycols. Reactor 338 may also include transition metals such as iron, cobalt, and ruthenium as well as other transition metal oxides as catalysts, on inorganic support structures that may promote the reaction of CO with hydrogen at lower temperatures and pressures.

Second region 118 may co-produce formaldehyde 312 from methanol 304 reactant. It is contemplated that methanol 304 may include methanol or any other alcohol such as ethanol, 2-propanol, phenol, 1-propanol, 1-butanol, 2-butanol, isopropanol, benzyl alcohol, and allyl alcohol without departing from the scope or intent of the present disclosure. Formaldehyde 312 may also refer to any type of aldehyde or a carboxylic acid, including for example formic acid, acetaldehyde, acetic acid, 2-propanone (acetone), hydroquinone, 1-2 dihydrobenzene (catechol), 2,5 cyclohexadiene-1-one, benzoquinone, maleic acid, oxalic acid, propionaldehyde, propanoic acid, butyraldehyde, butanoic acid, butanone, acetone, benzaldehyde, benzoic acid, acrolein, and acrylic acid, without departing from the scope or intent of the present disclosure.

Referring to FIG. 4, first region 116 may produce a first product of carbon monoxide 410 which is combined with water 432 in a reactor 430 which may perform a water gas shift reaction. The water gas shift reaction performed by reactor 430 may produce carbon dioxide 434 and $H_2$ 436. Carbon monoxide 410 and $H_2$ 436 may be combined at reactor 438. Reactor 438 may cause a reaction, such as a Fischer-Tropsch synthesis, to reduce carbon monoxide to methane, methanol, hydrocarbons, glycols, olefins by utilizing $H_2$ 436. Carbon dioxide 434 may be a byproduct of water gas shift reaction of reactor 430 and may be recycled as an input feed to the first region 116. Reactor 438 may also include transition metals such as iron, cobalt, and ruthenium as well as other transition metal oxides as catalysts, on inorganic support structures that may promote the reaction of CO with hydrogen at lower temperatures and pressures.

Second region 118 may co-produce formaldehyde 412 from methanol 404 reactant. It is contemplated that methanol 404 may include methanol or another alcohol such as ethanol, 2-propanol, phenol, 1-propanol, 1-butanol, 2-butanol, isopropanol, benzyl alcohol, and allyl alcohol without departing from the scope or intent of the present disclosure. Formaldehyde 412 may also refer to any type of aldehyde or a carboxylic acid, including for example formic acid, acetaldehyde, acetic acid, 2-propanone (acetone), hydroquinone, 1-2 dihydrobenzene (catechol), 2,5 cyclohexadiene-1-one, benzoquinone, maleic acid, oxalic acid, propionaldehyde, propanoic acid, butyraldehyde, butanoic acid, butanone, acetone, benzaldehyde, benzoic acid, acrolein, and acrylic acid, without departing from the scope or intent of the present disclosure.

Figure 5:
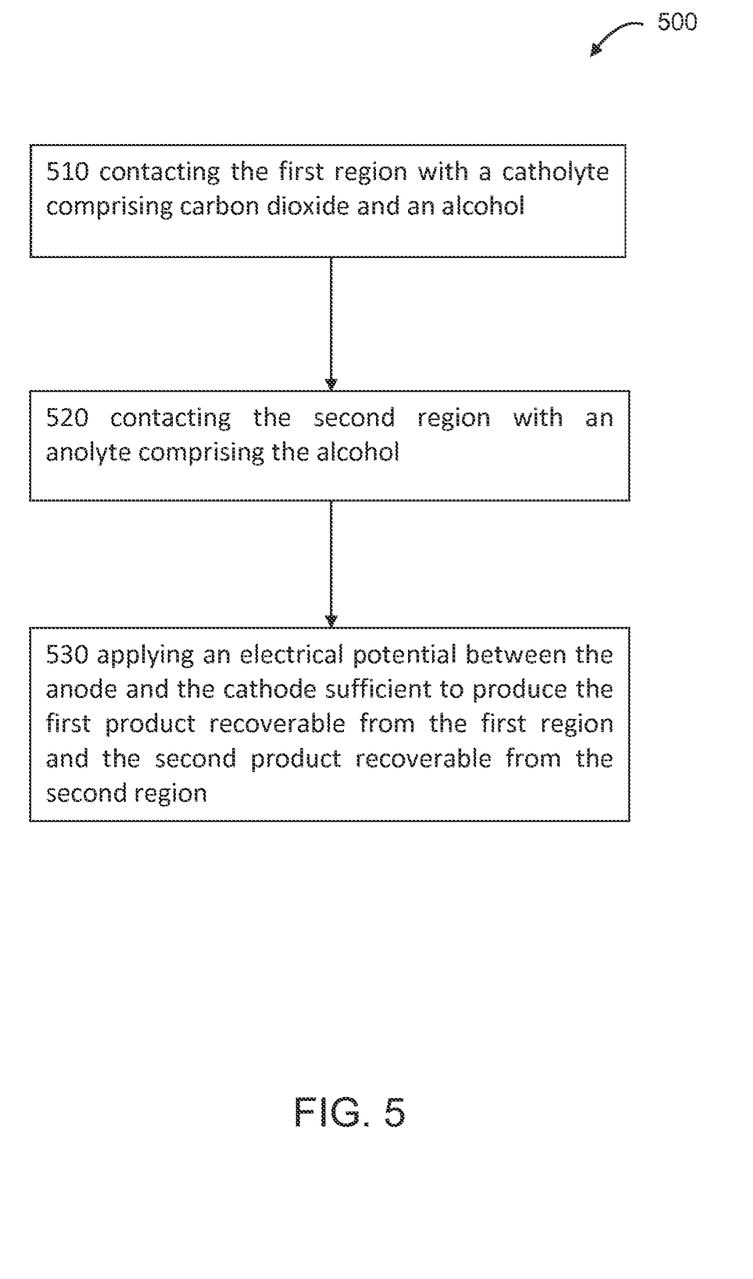
FIG. 5 is a flow diagram of a method of electrochemical co-production of products in accordance with an embodiment of the present disclosure.

Referring to FIG. 5 a flow diagram of a method 500 of electrochemical co-production of products in accordance with an embodiment of the present disclosure is shown. It is contemplated that method 500 may be performed by system 100 and system 200 as shown in FIGS. 1A, 1B, and 2. Method 500 may include producing a first product from a first region of an electrochemical cell having a cathode and a second product from a second region of the electrochemical cell having an anode.

Method 500 of electrochemical co-production of products may include a step of contacting the first region with a catholyte comprising carbon dioxide and an alcohol 510. Next, method 500 may include the step of contacting the second region with an anolyte comprising alcohol 520. The method 500 may further include the step of applying an electrical potential between the anode and the cathode sufficient to produce the first product recoverable from the first region and the second product recoverable from the second region. Advantageously, a first product produced at the first region may be recoverable from the first region and a second product produced at the second region may be recoverable from the second region.

Figure 6:
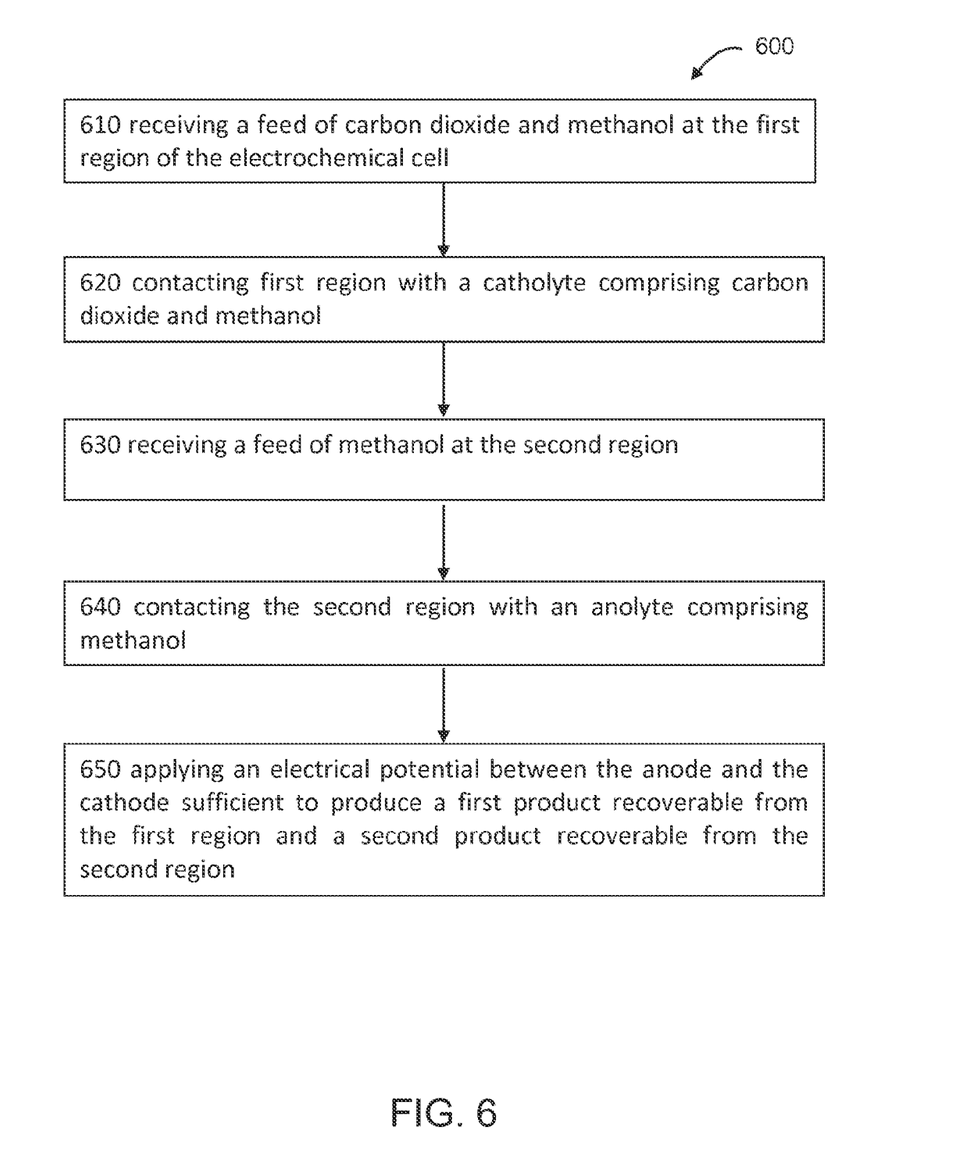
FIG. 6 is a flow diagram of a method of electrochemical co-production of products in accordance with another embodiment of the present disclosure.

Referring to FIG. 6 a flow diagram of a method 600 of electrochemical co-production of products in accordance with an embodiment of the present disclosure is shown. It is contemplated that method 600 may be performed by system 100 and system 200 as shown in FIGS. 1A, 1B, and 2. Method 600 may include steps for producing a first product from a first region of an electrochemical cell having a cathode and a second product from a second region of the electrochemical cell having an anode.

Method 600 may include the step of receiving a feed of carbon dioxide and methanol at the first region of the electrochemical cell 610. A further step of method 600 may include contacting the first region with a catholyte comprising carbon dioxide and methanol 620. The method 600 also includes the step of receiving a feed of methanol at the second region of the electrochemical cell 630 and contacting the second region with an anolyte comprising methanol 610. The method also includes the step of applying an electrical potential between the anode and the cathode sufficient to produce the first product recoverable from the first region and the second product recoverable from the second region 650.

It is contemplated that receiving a feed may include various mechanisms for receiving a supply of a reactant, whether in a continuous, near continuous or batch portions. Similarly, the reactant (such as the alcohol or carbon dioxide) may be jointly fed with additional reactants, the anolyte or catholyte, or may be fed separately into either the first region or second region.

It is further contemplated that the structure and operation of the electrochemical cell may be adjusted to provide desired results. For example, the electrochemical cell may operate at higher pressures, such as pressures above atmospheric pressure which may increase current efficiency and allow for operation of the electrochemical cell at higher current densities.

The first product and the second product may be mixed with other products. For example, the second product may include a methanol/formaldehyde mixture, or a methanol/carboxylic acid mixture. These mixtures may be separated outside of the electrochemical cell using conventional separation techniques, including distillation and esterification.

In one embodiment, the Faradaic current efficiency of the anode could be between 90 to 100%, and the acetate Faradaic current efficiency could be between 25 and 100%. The flow circulation of the anolyte and catholyte is such that it provides sufficient flow for the reactions. The flow rate may be varied to select for the production of different products, such as formaldehyde instead of formic acid, CO, and $CO_2$ from methanol oxidation.

Additionally, the cathode and anode may comprise a high surface area with a void volume which may range from 30% to 98%. The surface area may be from 2 $cm^2/cm^3$ to 500 $cm^2/cm^3$ or higher. It is contemplated that surface areas also may be defined as a total area in comparison to the current distributor/conductor back plate, with a preferred range of 2× to 1000× or more.

The anode may comprise a polymeric bound carbon current distributor anode employing a carbon felt with a specific surface area of 50 $cm^2/cm^3$ or more that fills the gap between a cathode backplate and the membrane, resulting in a zero gap anode.

The cathode may comprise a number of high surface area materials to include copper, stainless steels, carbon, and silicon, which may be further coated with a layer of material which may be a conductive metal or semiconductor. A very thin plastic screen may be incorporated against the cathode side of the membrane to prevent the membrane from touching the high surface area cathode structure. The high surface area cathode structure may be mechanically pressed against the cathode current distributor backplate, which may be composed of material that has the same surface composition as the high surface area cathode. For electrochemical reductions, the cathode electrode may be a suitable conductive electrode, such as Al, Au, Ag, Bi, C, Cd, Co, Cr, Cu, Cu alloys (e.g., brass and bronze), Ga, Hg, In, Mo, Nb, Ni, $NiCo_2O_4$, Ni alloys (e.g., Ni 625, NiHX), Ni—Fe alloys, Pb, Pd alloys (e.g., PdAg), Pt, Pt alloys (e.g., PtRh), Rh, Sn, Sn alloys (e.g., SnAg, SnPb, SnSb), Ti, V, W, Zn, stainless steel (SS) (e.g., SS 2205, SS 304, SS 316, SS 321), austenitic steel, ferritic steel, duplex steel, martensitic steel, Nichrome (e.g., NiCr 60:16 (with Fe)), elgiloy (e.g., Co—Ni—Cr), degenerately doped n-Si:As, degenerately doped n-Si:As, degenerately doped n-Si: B, degenerately doped n-Si, degenerately doped n-Si:As, and degenerately doped n-Si:B. Other conductive electrodes may be implemented to meet the criteria of a particular application. For photoelectrochemical reductions, the electrode may be a p-type semiconductor, such as p-GaAs, p-GaP, p-InN, p-InP, p-CdTe, p-GaInP$_2$ and p-Si, or an n-type semiconductor, such as n-GaAs, n-GaP, n-InN, n-InP, n-CdTe, n-GaInP$_2$ and n-Si. Other semiconductor electrodes may be implemented to meet the criteria of a particular application including, but not limited to, CoS, $MoS_2$, TiB, $WS_2$, SnS, $Ag_2S$, $CoP_2$, $Fe_3P$, $Mn_3P_2$, MoP, $Ni_2Si$, $MoSi_2$, $WSi_2$, $CoSi_2$, $Ti_4O_7$, $SnO_2$, GaAs, GaSb, Ge, and CdSe.

Catholyte may include a pH range from 1 to 12, and more specifically from 4 to 10. The pH may be a function of the desired product and whether any catalysts are utilized in operation of the electrochemical cell. Preferably, catholyte and catalysts may be selected to prevent corrosion at the electrochemical cell. Catholyte may include homogeneous catalysts such as pyridine, 2-picoline, and the like. Catholyte electrolytes may include alkali metal bicarbonates, carbonates, sulfates, phosphates, borates, and hydroxides. Non-aqueous solvents, such as propylene carbonate, methanesulfonic acid, methanol, and other ionic conducting liquids may be used rather than water. The electrolyte may comprise one or more of $Na_2SO_4$, KCl, $NaNO_3$, NaCl, NaF, $NaClO_4$, $KClO_4$, $K_2SiO_3$, $CaCl_2$, a guanidinium cation, a H cation, an alkali metal cation, an ammonium cation, an alkylammonium cation, a tetraalkyl ammonium cation, a halide anion, an alkyl amine, a borate, a carbonate, a guanidinium derivative, a nitrite, a nitrate, a phosphate, a polyphosphate, a perchlorate, a silicate, a sulfate, and a hydroxide.

The catholyte may comprise a homogeneous catalyst. Homogeneous catalysts comprising aromatic heterocyclic amines may include, but are not limited to, unsubstituted and substituted pyridines and imidazoles. Substituted pyridines and imidazoles may include, but are not limited to mono and disubstituted pyridines and imidazoles. For example, suitable catalysts may include straight chain or branched chain lower alkyl (e.g., $C_1$-$C_{10}$) mono and disubstituted compounds such as 2-methylpyridine, 4-tertbutyl pyridine, 2,6 dimethylpyridine (2,6-lutidine); bipyridines, such as 4,4'-bipyridine; amino-substituted pyridines, such as 4-dimethylamino pyridine; and hydroxyl-substituted pyridines (e.g., 4-hydroxy-pyridine) and substituted or unsubstituted quinoline or isoquinoline. The catalysts may also suitably substituted or unsubstituted dinitrogen heterocyclic amines, such as pyrazine, pyridazine and pyrimidine. Other catalysts generally include azoles, imidazoles, indoles, oxazoles, thiazoles, substituted species and complex multi-ring amines such as adenine, pterin, pteridine, benzimidazole, phenanthroline and the like.

In one embodiment, a catholyte/anolyte flow rate may include a catholyte/anolyte cross sectional area flow rate range such as 2-3,000 gpm/ft$^2$ or more (0.0076-11.36 m$^3$/m$^2$). A flow velocity range may be 0.002 to 20 ft/sec (0.0006 to 6.1 m/sec). Operation of the electrochemical cell catholyte at a higher operating pressure allows more dissolved carbon dioxide to dissolve in the aqueous solution. Typically, electrochemical cells can operate at pressures up to about 20 to 30 psig in multi-cell stack designs, although with modifications, the electrochemical cells may operate at up to 100 psig. The electrochemical cell may operate anolyte at the same pressure range to minimize the pressure differential on a separator or membrane separating the cathode and the anode. Special electrochemical designs may be employed to operate electrochemical units at higher operating pressures up to about 60 to 100 atmospheres or greater, which is in the liquid $CO_2$ and supercritical $CO_2$ operating range.

The catholyte may be operated at a temperature range of −10 to 95° C., more preferably 5-60° C. The lower temperature will be limited by the catholytes used and their freezing points. In general, the lower the temperature, the higher the solubility of $CO_2$ in the aqueous solution phase of the catholyte, and would help in obtaining higher conversion and current efficiencies. The drawback is that the operating electrochemical cell voltages may be higher, so there is an optimization that would be done to produce the chemicals at the lowest operating cost. In addition, the catholyte may require cooling, so an external heat exchanger may be employed, flowing the catholyte through the heat exchanger and using cooling water to remove the heat and control the catholyte temperature.

The anolyte operating temperatures may be in the same ranges as the ranges for the catholyte, and may be in a range of 0° C. to 95° C. In addition, the anolyte may require cooling, so an external heat exchanger may be employed, flowing the anolyte through the heat exchanger and using cooling water to remove the heat and control the anolyte temperature.

Electrochemical cells may include various types of designs. These designs may include Zero Gap, flow-through with a recirculating catholyte electrolyte with various high surface area cathode materials. The electrochemical cell may include flooded co-current packed and trickle bed designs with the various high surface area cathode materials. Also, bipolar stack cell designs and high pressure cell designs may also be employed for the electrochemical cells.

Anodes may include electrocatalytic coatings applied to the surfaces of the base anode structure. For example, for acid anolytes and oxidizing water generating oxygen, the preferred electrocatalytic coatings may include precious metal oxides such as ruthenium and iridium oxides, as well as platinum and gold and their combinations as metals and oxides on valve metal substrates such as titanium, tantalum, zirconium, or niobium. For bromine and iodine anode chemistry, carbon and graphite are particularly suitable for use as anodes. Polymeric bonded carbon materials may also be used. For other anolytes comprising alkaline or hydroxide electrolytes, anodes may include carbon, cobalt oxides, stainless steels, transition metals, and their alloys and combinations. High surface area anode structures that may be used which would help promote the reactions at the anode surfaces. The high surface area anode base material may be in a reticulated form composed of fibers, sintered powder, sintered screens, and the like, and may be sintered, welded, or mechanically connected to a current distributor back plate that is commonly used in bipolar cell assemblies. In addition, the high surface area reticulated anode structure may also contain areas where additional applied catalysts on and near the electrocatalytic active surfaces of the anode surface structure to enhance and promote reactions that may occur in the bulk solution away from the anode surface such as the reaction between bromine and the carbon based reactant being introduced into the anolyte. The anode structure may be gradated, so that the density of the may vary in the vertical or horizontal direction to allow the easier escape of gases from the anode structure. In this gradation, there may be a distribution of particles of materials mixed in the anode structure that may contain catalysts for the bulk reaction of the carbon based reactant.

The separator, also referred as a membrane, between the cathode and the anode, may include cation ion exchange type membranes. Cation ion exchange membranes which have an high rejection efficiency to anions may be preferred. Examples of such cation ion exchange membranes may include perfluorinated sulfonic acid based ion exchange membranes such as DuPont Nafion brand unreinforced types N117 and N120 series, more preferred PTFE fiber reinforced N324 and N424 types, and similar related membranes manufactured by Japanese companies under the supplier trade names such as AGC Engineering (Asahi Glass) under their trade name Flemion®. Other multi-layer perfluorinated ion exchange membranes used in the chlor alkali industry may have a bilayer construction of a sulfonic acid based membrane layer bonded to a carboxylic acid based membrane layer, which efficiently operates with an anolyte and catholyte above a pH of about 2 or higher. These membranes may have an higher anion rejection efficiency. These are sold by DuPont under their Nafion® trademark as the N900 series, such as the N90209, N966, N982, and the 2000 series, such as the N2010, N2020, and N2030 and all of their types and subtypes. Hydrocarbon based membranes, which are made from of various cation ion exchange materials can also be used if the anion rejection is not as desirable, such as those sold by Sybron under their trade name Lonac®, Engineering (Asahi Glass) under their trade name Selemion®, and Tokuyama Soda, among others on the market. Ceramic based membranes may also be employed, including those that are called under the general name of NASICON (for sodium super-ionic conductors) which are chemically stable over a wide pH range for various chemicals and selectively transports sodium ions, the composition is $Na_{1+x}Zr_2Si_xP_3-xO_{12}$, and well as other ceramic based conductive membranes based on titanium oxides, zirconium oxides and yttrium oxides, and beta aluminum oxides. Alternative membranes that may be used are those with different structural backbones such as polyphosphazene and sulfonated polyphosphazene membranes in addition to crown ether based membranes. Preferably, the membrane or separator is chemically resistant to the anolyte and catholyte. Preferably, the membrane or separator is chemically resistant to the anolyte and catholyte and operates at temperatures of less than 600 degrees C., and more preferably less than 500 degrees C.

A catholyte or an anolyte may comprise an aqueous solvent, a non-aqueous solvent, or a mixture of solvents containing one or more of water as well as protic or aprotic polar solvents such as methanol, ethanol, acetonitrile, propylene carbonate, ethylene carbonate, dimethyl carbonate, diethyl carbonate, dimethylsulfoxide, dimethylformamide, acetonitrile, acetone, tetrahydrofuran, N,N-dimethylacetamide, dimethoxyethane, diethylene glycol dimethyl ester, butyronitrile, 1,2-difluorobenzene, γ-butyrolactone, N-methyl-2-pyrrolidone, sulfolane, 1,4-dioxane, nitrobenzene, nitromethane, acetic anhydride, and ionic liquids. An aqueous solvent comprises at least 5% water. A non-aqueous solvent comprises less than 5% water.

The rate of the generation of the second product formed in the second region from the anode reaction, such as the oxidation of methanol to formaldehyde, is contemplated to be proportional to the applied Faradaic current to the electrochemical cell. The rate of the input or feed of the carbon based reactant into the second region should then be fed in proportion to the applied Faradaic current or amperage rate to the electrochemical cell. The anode reaction efficiency would determine the maximum theoretical formation in moles of the alcohol oxidation product at the applied current. It is contemplated that the molar ratio of alcohol feed to the theoretical moles of potentially formed alcohol oxidation product would be in a range of 500:1 to 2:1, and preferably in the range of 200:1 to 10:1, where the alcohol is in excess of the theoretical required for the anode reaction. In this contemplated mode of operation, there is an excess of alcohol in the anolyte during operation. The operation of an extractor and its selected separation method—for example fractional distillation—the actual products produced, and the selectivity of the wanted reaction would determine the optimum molar ratio of the carbon based reactant to the applied Faradaic current rate applied in the second region. Any of the unreacted components could be recycled to the second region.

Similarly, the rate of the generation of the formed electrochemical carbon dioxide reduction product in the first (catholyte) compartment, such as CO, is contemplated to be proportional to the applied current to the electrochemical cell. The rate of the input or feed of the carbon dioxide source into the first compartment should be fed in a proportion to the applied current. The cathode reaction efficiency would determine the maximum theoretical formation in moles of the carbon dioxide reduction product at the applied current. It is contemplated that the ratio of carbon dioxide feed to the theoretical moles of potentially formed carbon dioxide reduction product based on the applied current, would be in a range of 100:1 to 2:1, and preferably in the range of 50:1 to 5:1, where the carbon dioxide is in excess of the theoretical required for the cathode reaction. The carbon dioxide excess would then be separated in the extractor and recycled back to the second compartment.

In the present disclosure, the methods disclosed may be implemented as sets of instructions or software readable by a device. Further, it is understood that the specific order or hierarchy of steps in the methods disclosed are examples of exemplary approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:

1. A method for producing a first product from a first region of an electrochemical cell having a cathode and a second product from a second region of the electrochemical cell having an anode, the method comprising the steps of:

contacting the first region with a catholyte comprising carbon dioxide;

contacting the second region with an anolyte, the anolyte comprising an alcohol, the anolyte comprising the alcohol is in a gaseous phase; and applying an electrical potential between the anode and the cathode sufficient to produce the first product recoverable from the first region and the second product recoverable from the second region, the anode including a metal substrate and an electrocatalytic coating on the metal substrate, the metal substrate includes at least one of titanium, tantalum, zirconium or niobium and the electrocatalytic coating includes a metal oxide, the metal oxide includes at least one of ruthenium, iridium, platinum or gold.

2. The method according to claim 1, wherein the anolyte is free of halide ions.

3. The method according to claim 1, wherein the alcohol includes at least one of methanol, ethanol, ethylene glycol, glycerol, 1-propanol, 2-propanol, phenol, 1-butanol, 2-butanol, isopropanol, benzyl alcohol, allyl alcohol, a glycol, or a polyol.

4. The method according to claim 1, wherein the cathode and the anode are separated by an ion permeable barrier.

5. The method according to claim 4, wherein the ion permeable barrier includes at least one of a solid polymer conductor electrolyte material, a perfluorinated sulfonic acid based membrane, a sodium super-conducting ionic conductor ceramics, zirconium-yttria ceramics or beta-alumina based ceramics.

6. The method according to claim 1, wherein the anode including the electrocatalytic coating is configured for oxidation of the alcohol.

7. The method according to claim 1, wherein the catholyte further comprises an electrolyte.

8. The method according to claim 7, wherein the electrolyte includes at least one of alkali metal bicarbonate, carbonate, sulfate, phosphate or borate.

9. The method according to claim 1, wherein the catholyte further comprises a homogeneous catalyst.

10. The method according to claim 9, wherein the homogeneous catalyst includes an aromatic heterocyclic amine.

11. The method according to claim 1, wherein the catholyte further comprises said alcohol.

12. The method of claim 1, wherein a molar ratio of alcohol to the second product is in a range of 500:1 to 2:1.

13. A method for producing a first product from a first region of an electrochemical cell having a cathode and a second product from a second region of the electrochemical cell having an anode, the method comprising the steps of:

contacting the first region with a catholyte comprising carbon dioxide;

contacting the second region with an anolyte, the anolyte comprising an alcohol, the anolyte comprises an aqueous solution of the alcohol, the aqueous solution of the alcohol includes at least 5% water; and applying an electrical potential between the anode and the cathode sufficient to produce the first product recoverable from the first region and the second product recoverable from the second region, the anode including a metal substrate and an electrocatalytic coating on the metal substrate, the metal substrate includes at least one of titanium, tantalum, zirconium or niobium and the electrocatalytic coating includes a metal oxide, the metal oxide includes at least one of ruthenium, iridium, platinum or gold.

14. The method according to claim 13, wherein the anolyte is free of halide ions.

15. The method according to claim 13, wherein the alcohol includes at least one of methanol, ethanol, ethylene glycol, glycerol, 1-propanol, 2-propanol, phenol, 1-butanol, 2-butanol, isopropanol, benzyl alcohol, allyl alcohol, a glycol, or a polyol.

16. The method according to claim 13, wherein the cathode and the anode are separated by an ion permeable barrier.

17. The method according to claim 16, wherein the ion permeable barrier includes at least one of a solid polymer conductor electrolyte material, a perfluorinated sulfonic acid based membrane, a sodium super-conducting ionic conductor ceramics, zirconium-yttria ceramics or beta-alumina based ceramics.

18. The method according to claim 13, wherein the anode including the electrocatalytic coating is configured for oxidation of the alcohol.

19. The method according to claim 13, wherein the catholyte further comprises an electrolyte.

20. The method according to claim 19, wherein the electrolyte includes at least one of alkali metal bicarbonate, carbonate, sulfate, phosphate or borate.

21. The method according to claim 13, wherein the catholyte further comprises a homogeneous catalyst.

22. The method according to claim 21, wherein the homogeneous catalyst includes an aromatic heterocyclic amine.

23. The method according to claim 13, wherein the catholyte further comprises said alcohol.

24. The method of claim 13, wherein a molar ratio of alcohol to the second product is in a range of 500:1 to 2:1.

* * * * *